US008277492B2

(12) United States Patent
Williams (10) Patent No.: US 8,277,492 B2
(45) Date of Patent: Oct. 2, 2012

(54) BONE ANCHORED SURGICAL MESH (75) Inventor: Lytton A. Williams, Rolling Hills Estates, CA (US)

(73) Assignee: Onike Technologies, Rolling Hills Estates, CA (US)

( * ) Notice: Subject to any disclaimer, the term of this patent is extended or adjusted under 35 U.S.C. 154(b) by 0 days.

(21) Appl. No.: 12/890,375

(22) Filed: Sep. 24, 2010

(65) Prior Publication Data

US 2011/0035008 A1 Feb. 10, 2011

Related U.S. Application Data (62) Division of application No. 11/408,578, filed on Apr. 21, 2006, now Pat. No. 7,824,433.

(60) Provisional application No. 60/677,686, filed on May 3, 2005.

(51) Int. Cl.
*A61B 17/80* (2006.01)

(52) U.S. Cl. .......... 606/283; 606/284; 606/285; 606/298

(58) Field of Classification Search .......... 606/283–285, 606/298
See application file for complete search history.

(56) References Cited

U.S. PATENT DOCUMENTS

| 5,261,910 | A | * | 11/1993 | Warden et al. ................. 606/292 |
|-----------|---|---|---------|----------------------------------------|
| 5,346,492 | A |   | 9/1994  | Morgan |
| 5,366,455 | A |   | 11/1994 | Dove et al. |
| 5,368,602 | A |   | 11/1994 | de la Torre |
| 5,437,672 | A |   | 8/1995  | Alleyne |
| 5,611,354 | A | * | 3/1997  | Alleyne ................. 128/846 |
| 5,676,666 | A |   | 10/1997 | Oxland et al. |
| 5,743,913 | A |   | 4/1998  | Wellisz |
| 5,954,722 | A | * | 9/1999  | Bono ................. 606/281 |
| 7,824,433 | B2 |  | 11/2010 | Williams |
| 2002/0123750 | A1 | * | 9/2002 | Eisermann et al. .......... 606/69 |
| 2002/0133155 | A1 | * | 9/2002 | Ferree ................. 606/61 |
| 2003/0065401 | A1 |   | 4/2003 | Amrich et al. |
| 2003/0078588 | A1 |   | 4/2003 | Alleyne |
| 2005/0149032 | A1 |   | 7/2005 | Vaughen et al. |
| 2006/0224242 | A1 |   | 10/2006 | Swords et al. |

FOREIGN PATENT DOCUMENTS

| JP | 2004537337 T | 12/2004 |
| WO | 95/20368 | 8/1995 |
| WO | 02067824 A2 | 9/2002 |
| WO | 03/101319 A2 | 12/2003 |

OTHER PUBLICATIONS

European Patent Office Extended European Search Report dated Mar. 30, 2009.

* cited by examiner

*Primary Examiner* — Eduardo C Robert
*Assistant Examiner* — Julianna N Harvey
(74) *Attorney, Agent, or Firm* — Steinfl & Bruno LLP (57) ABSTRACT

A bone-anchored surgical mesh has slot-like anchoring members that allow for the variable placement of screws and other bone fasteners. This permits the surgeon discretion in the placement of bone fasteners used to attach the mesh to the patient's bone. The elongate openings of the anchoring members allow for a sliding motion between the bone fasteners and the anchoring members, and facilitates positioning and articulation of the mesh. The anchoring members may include bushings to aid the sliding motion of the anchoring member on the bone fastener. In one embodiment, the mesh consists of shorter modular strips that overlap each other such that a single bone fastener is passed through two overlapping anchoring members to lock the two modular mesh strips together. Additional modular mesh strips can be added on at either end, as desired, to provide the desired length of dural coverage.

47 Claims, 4 Drawing Sheets

BONE ANCHORED SURGICAL MESH

REFERENCE TO PENDING PRIOR PATENT APPLICATIONS

This is a divisional of prior U.S. patent application Ser. No. 11/408,578, filed Apr. 21, 2006 now U.S. Pat. No. 7,824,433 by Lytton A. Williams for BONE ANCHORED SURGICAL MESH, which in turn claims the benefit under 35 U.S.C. 119(e) of U.S. Provisional Patent Application Ser. No. 60/677,686, filed May 3, 2005, by Lytton A. Williams. The above-identified patent applications are hereby incorporated herein by reference.

FIELD OF THE INVENTION

The present invention relates generally to orthopedic devices. More specifically, the present invention relates to orthopedic devices that are fastened to bone such as surgical meshes and spinal implants useful for covering, replacing, and supporting spinal elements.

BACKGROUND OF THE INVENTION

Spinal surgery is a common medical procedure in the United States and throughout the world. Spinal surgery is typically performed to decompress nerves and/or to stabilize the spinal elements. Spinal surgery can involve either anterior or posterior approaches to the spine. There are variations in the spinal anatomy of the cervical, thoracic, and lumbar levels of the spine. However, there are common anatomical elements of the spine at all the levels. The anterior bone elements of the spine include the vertebral bodies, with the interposed intervertebral discs. The posterior bone elements of the spine include the lamina, the spinous processes, the facet joints, the pedicles, and the transverse processes. Several ligaments, including the anterior longitudinal ligament, the posterior longitudinal ligament, the ligamentum flavum (or interlaminar ligament) and the interspinous ligament provide fibrous connections between the bone elements and contribute to the mechanical stability of the spine.

The neural elements, which include the spinal cord, the cauda equina, and the nerve roots, are covered by the dura and is positioned within the spinal canal. The lamina provides a posterior bony roof over the spinal canal and the dura. The lamina protects the neural elements in the spinal canal and also contributes to the mechanical stablility of the spine. The interspinous ligaments and ligamentum flavum (together referred to herein as the posterior ligaments), the spinous processes, and the lamina are important in contributing to the mechanical stability to the spine, especially in forward flexion of the spine.

One of the most common types of spinal surgery involves decompression of the neural elements within the spinal canal. Decompression of the neural elements commonly necessitates removal of all or part of the lamina and the posterior ligaments and is referred to as a laminectomy. Decompression laminectomy involves the removal of the lamina, spinous processes, and posterior ligaments, thereby exposing the dura and nerve roots. After a decompression laminectomy, scar tissue typically forms over the dura and only the skin and posterior spinal muscles protect the neural elements. The neural elements become more vulnerable to traumatic injuries after surgery. Furthermore, laminectomy can result in the compromise of spinal stability, leading to spinal deformity, pain, and neurologic problems including myelopathy or nerve root symptoms.

Following a laminectomy, subsequent spinal operations and revision surgeries are much more difficult than a first surgery on the spine. Scar tissue forming over the dura is a significant problem after surgery and frequently a cause of further spinal pathology symptoms. Because of scar tissue formation, subsequent surgeries are more difficult because of a lack of clear anatomic boundaries between the dura and other soft tissues. Scar tissue commonly forms dense adhesions to the dura. Very careful dissection is therefore required in revision spinal surgery to expose the dura and to separate the dura from the other surrounding tissues. It is not uncommon to injure the dura during these subsequent surgeries, thereby resulting in leakage of spinal fluids and sometimes injury to the neural elements. Various dural coverings and soft tissue grafts have been utilized in the past, however, these coverings are simple sheets that are laid over the dura and that are not anchored to the bone. These coverings can move out of place during wound closure or subsequent removal of deep surgical suction drains. Soft coverings do not provide any significant protection to the dura from penetrating trauma. During subsequent surgical procedures, a simple overlay covering would provide little resistance to pressure from surgical instruments. Also, these sheet-like dural coverings and soft tissue grafts frequently do not result in a clearly defined dissection plane between the dura and the other posterior soft tissues during subsequent surgery.

Decompression laminectomy, particularly in the cervical spine, can result in spinal instability, leading to spinal deformity, pain, and neurologic problems including myelopathy. The lamina and posterior ligaments play an important part in the stability of the cervical spine. It is well known that after cervical laminectomy, a certain percentage of patients will develop a flexion deformity of the spine. Because of this, many surgeons have opted for an anterior approach to decompression of the cervical spine. However, the anterior approaches require a spinal fusion that limits functional mobility of the cervical spine thereafter. Some surgeons, especially in Japan, remove the cervical lamina en bloc and then reattach the cervical lamina back to the spine using sutures or wires in a manner that expands the spinal canal. This procedure is known as laminoplasty. During laminoplasty, the lamina is reattached in a fashion that expands the spinal canal and decompresses the spinal cord. Usually, bone grafts are positioned between the lamina and facets prior to reattachment of the lamina in order to achieve a more expansive spinal canal. Bone growth slowly results in bony reattachment of the removed lamina back to the spine. Several surgeons have reported that laminoplasty helps prevent the development of post-laminectomy cervical spinal deformity. However, the procedure of laminoplasty can be technically challenging, because removal of the lamina en bloc is difficult, and runs the risk that the lamina will move out of place during healing, resulting in compression of the spinal cord.

Another procedure that is performed on the spine is spinal fusion. Spinal fusion can be anterior or posterior. One method of performing a posterior fusion, especially on the cervical spine includes placing a bone graft between the lamina of adjacent spinal levels. The bone graft must be held in place until bony healing and fusion takes place. The bone graft is commonly secured with wires passed under the adjacent lamina. However, this procedure can be dangerous because the spinal canal must be entered when passing the wire underneath the lamina. Pressure on the spinal cord can result in quadriplegia. The method of performing an anterior spinal fusion involves removal of the intervertebral disc and placement of a bone graft. Frequently a plate is attached to the vertebra on either side of the bone graft, to secure that the bone graft does not extrude anteriorly and to prevent motion while the bone graft heals into place.

A recent development in spinal surgery is the implantation of artificial spinal discs. One example of an artificial disc replacement is the Charite artificial disc available from DePuy Spine, Inc. located in Raynham, Mass., USA. Artificial discs may be advantageous in treating disc disease while maintaining spinal motion. A spinal level that is fused is rigid and places increased mechanical stresses on the adjacent spinal disc levels, thereby accelerating the development of degenerative disc disease at the adjacent spinal disc levels. An artificial disc may be more advantageous than a fusion because the artificial disc allows motion at a disc space where it is inserted. Use of a rigid anterior or posterior spinal plate over a segment where an artificial disc is implanted would counteract the benefits of segmental motion provided by the artificial disc. Therefore, rigid posterior spinal instrumentation is usually not used in combination with an artificial disc. Furthermore, implantation of an artificial disc anteriorly between two vertebral bodies usually requires intact posterior spinal elements. Intact posterior spinal elements are important in preventing excessive distraction of the disc space during placement of an artificial disc and dislocation of the artificial disc post-operatively. Patients who have had lumbar laminectomy with removal of posterior elements, for example, the lamina, have therefore not been good candidates for total disc replacement with an artificial disc. It would be advantageous to stabilize the posterior elements while still permitting segmental spinal motion.

An older method of performing a fusion was a posterior midline fusion. This procedure involves placing bone graft on the lamina, adjacent to the midline of the spine. However, complications of extensive bone growth impinging on the neural elements was frequently reported and posterior midline fusion has been largely abandoned. Currently, BMP (Bone Morphogenic Protein) is available for use in the United States and elsewhere in the world. BMP encourages bone growth and the formation of a fusion mass. However, there is no present method or system for placing BMP in a controlled fashion, over exposed dura, after laminectomy. Present orthopedic plating systems are not presently designed to cover over the posterior midline of the spine to protect the dura.

Surgical meshes have been designed for a variety of non-orthopedic uses. Flexible surgical meshes are commonly used, for example, for hernia repair or vascular grafts. There are some meshes or mats that can be attached to bone. One known vertebral auxiliary fixation device has a holding mat and a plurality of fastening elements. Where a foreign object which is implanted in the vertebra, the holding mat is fastened to the vertebra such over the foreign object to prevent the implanted foreign object from jutting out of the vertebra. The holding mat and the fastening elements are made of a material capable of being assimilated into the tissues of a human body. Another known spine stabilization system is designed for application to the anterior spine, and includes a flexible member attachable to a portion of the spinal column. These devices require single points of screw fixation and do not permit sliding.

For the fixation of bone parts or for the bridging of bone defects, particularly in the region of the skull and jaw, it is also known to use a bridge made of biocompatible material with a reticular structure and with recesses for receiving bone screws. Each recess can be used for receiving a bone screw. The bridges do not permit sliding. Orthopedic implants can be made from a mesh material treated in order to promote bone growth, to provide antibiotics, or to provide other beneficial treatment. These devices require fixed anchoring holes for receiving a fastener, and do not permit sliding.

Meshes or mats containing round fixed holes for placement of screws do not give a surgeon flexibility or leeway in screw placement. The distance between adjacent anatomic points, such as a cervical or lumbar facet, will vary from patient to patient, and from one spinal level to another within a single patient. A device with fixed spacing of single round holes may not be capable of being aligned with a patient's anatomy to provide optimal fastening to a patients bone, or simply may not fit a particular patient or spinal level at all, because the patient's anatomy may not line up with the predetermined fixed round holes. Furthermore, fixed round holes do not permit a sliding or gliding motion upon the anchoring screws. Allowing some physiologic motions of the spine may be important in avoiding accelerated degenerative changes of the spine at the levels that are adjacent to a fixation device.

There is a need for a dural covering that will provide a dissection plane between the dura and the soft tissues and help inhibit the attachment of dense scar tissue adhesions to the dura. The dural covering would preferably be secured in place to the bone, so as to not move off of the dura during wound closure or removal of surgical drainage tubes. There is also a need for a posterior spinal implant that simulates the function of the posterior ligaments and lamina, thereby restoring some of the posterior stability to the spine. Still another need is for an anchored covering adapted for use with an interlaminar bone graft, thereby keeping the bone graft in position without having to pass sublaminar wires. There is a need is for an anchored covering over an implanted artificial disc to keep the artificial disc from extruding anteriorly while still permitting spinal motion at the operated disc level. Yet another need is for an anchored dural covering that provides a basic structural framework for the application of posterior bone graft, for example morcelated graft, or BMP (bone morphogenic protein). The structural framework would also preferably prevent bone growth from impinging upon and compressing the neural elements. Yet another recognized need is for a covering that can be slidably anchored to bone, thereby allowing ease of application of the covering and also allowing some physiologic movement of the vertebra. There is a need is for a covering that gives the surgeon leeway and discretion in placement of bone fasteners and that is capable of application to a variety of different patients and different spinal levels. Still another need is for a fenestrated mesh like structure that when covering the laminectomy defect will allow for drainage of blood out of the spinal canal so as to avoid the development of an epidural hematoma. The present invention fulfills these needs and others.

SUMMARY OF THE INVENTION

Briefly and in general terms, the present invention provides a surgical mesh covering that can be anchored to bone. Although described herein for application to the spine, application to other bony anatomic structures is also included in the invention. The surgical mesh provides elongated slot like anchoring members that receive bone screws or other bone fasteners. The elongated slots of the anchoring members of the mesh also provide for variable placement of the screws. In one aspect of the invention, an anchoring member slidable receives a bone fastener, such as a screw or a wire. The connection of the anchoring members, also referred to herein as anchoring slots, to the bone fasteners may further include bushings to aid the sliding motion of the anchoring member on the bone fastener.

In one aspect of the invention, the mesh is pliable and comprises a soft and flexible fabric like quality. An anchored covering for the dura or a bone graft is thereby provided. A soft and flexible quality mesh may be provided to make revision surgery easier by providing a dissection plane with the dura. A soft and flexible quality mesh may further be provided to perform as an artificial ligament.

In another aspect of the invention, the mesh is substantially rigid and comprises a firm and supportive quality. A rigid mesh provides a hard covering over the dura. A rigid mesh provides structural support for the spine and may also be used as a framework upon which bone graft or BMP may be applied. In other aspects of the invention, the mesh is semi-rigid and intermediate in structural characteristics between the pliable mesh and the rigid mesh.

In accordance with certain aspects of the present invention there is provided various types of fasteners to bone. In one aspect, a screw that is capable of locking to the bone is provided. Several types of locking bone screws are known in the art. In yet other aspects of the invention, a screw including a bushing is provided to aid sliding motion of the anchoring slot upon the screw. In yet other aspects of the invention, long or short, cortical or cancellous bone screws are provided. In still other aspects of the invention, the fastener to the bone may be a wire passing through the anchoring slot and the bone.

One other aspect of the invention is the ability of the device to secure a bone graft in place. The invention may be placed anteriorly over an interbody bone graft or artificial disc replacement and the bone fasteners secured to the vertebral bodies. The invention may also be placed posteriorly over an interlaminar graft, and the bone fasteners secured to the lamina or facets.

In one aspect of the invention, the mesh acts as a dural covering provides a dissection plane between the dura, the soft tissues, and scar tissue during revision surgery, and helps by acting as a barrier to inhibit the attachment of dense scar tissue adhesions to the dura. The mesh is secured in place to the bone, so as to not move out of position during wound closure or removal of surgical drainage tubes. The mesh may further provide a posterior spinal implant that simulates the function of the posterior ligaments and lamina, thereby restoring some of the posterior stability to the spine. In yet another aspect of the invention, the mesh provides an anchored covering of a interlaminar bone graft, thereby keeping the bone graft in position without having to pass sublaminar wires. In still another aspect of the invention, there is an anchored covering for an artificial disc, thereby keeping the artificial disc from extruding anteriorly while still permitting spinal motion at the operated disc level. Furthermore, in accordance with an aspect of the invention, there is provided an anchored dural covering that provides a basic structural framework for the application of posterior bone graft or BMP (bone morphogenic protein) and prevents bone growth from impinging upon and compressing the neural elements by providing a barrier between bone growth and the neural elements. Another aspect of the invention further provides a covering that can be slidably anchored to bone, thereby allowing ease of application of the covering and also allowing some physiologic movement of the vertebra by permitting sliding and gliding of elongated slot-like anchoring members upon bone fasteners. The elongated openings of the slot-like anchoring members can give the surgeon leeway and discretion in placement of bone fasteners and that is capable of application to a variety of different patients and different spinal levels. And in yet other aspects of the invention, the covering is fenestrated so that when covering the laminectomy defect the invention will allow for drainage of blood out of the spinal canal thereby avoiding the development of an epidural hematoma.

Another aspect of the invention is used in conjunction with total artificial disc replacement. Artificial discs may be advantageous in treating disc disease while maintaining segmental spinal motion at the disc level that is treated. Implantation of an artificial disc anteriorly between two vertebral bodies is preferred at a spinal level that has generally intact posterior spinal elements. Intact posterior spinal elements are important in preventing excessive distraction of the disc space during placement of an artificial disc and dislocation of the artificial disc post operatively. Patients who have had lumbar laminectomy with removal of posterior elements, for example, the lamina, have therefore previously not been good candidates for total disc replacement with an artificial disc. The present invention provides posterior stability while providing generally physiologic spinal motion, whereas a spinal fusion prevents segmental spinal motion. Therefore, when used in conjunction with the present invention, a patient who has had a laminectomy may still be a candidate for artificial disc replacement. Furthermore, because aspects of the invention allow continued segmental spinal motion, accelerated degeneration of adjacent disc levels may be prevented. One important aspect of the invention is that it provides improved rotational stability to the spine after a laminectomy.

Yet another aspect of the present invention is the use of tension bands that may be placed from one vertebral segment to another vertebral segment. The tension bands may be relatively rigid or relatively elastic. According to one aspect of the invention, at least one tension band may run between two or more bone screws or bone fasteners. The tension bands may be used in concert with the spinal mesh to adjust the amount of segmental motion permitted in the part of the spine to be treated. The tension bands may be useful to limit the degree of distraction of spinal segments or to limit the amount of flexion of spinal segments. In one aspect of the invention, the tension bands may be used without the spinal mesh.

Other features and advantages of the invention will become more apparent from the following detailed description of preferred embodiments of the invention, when taken in conjunction with the accompanying exemplary drawings.

DETAILED DESCRIPTION OF EMBODIMENTS OF THE INVENTION

Figure 1:
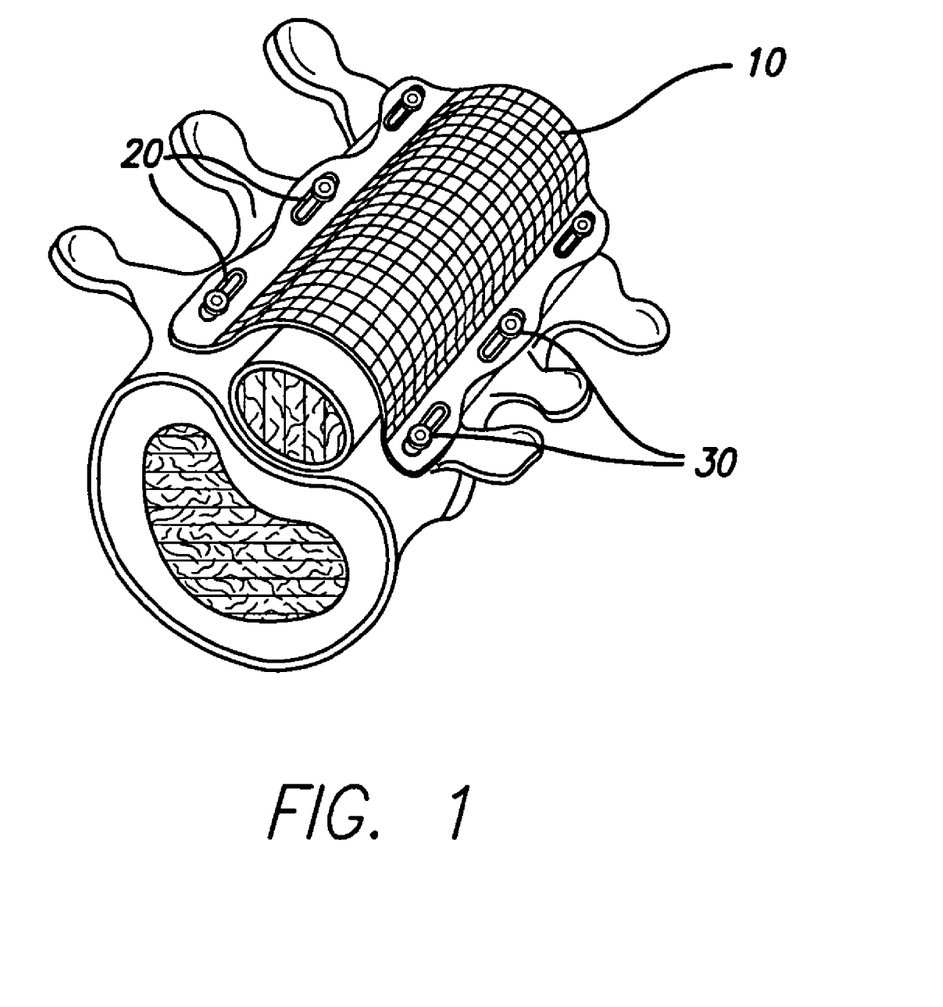
FIG. 1 is a perspective view of one embodiment of the invention showing a surgical mesh with elongated slot-like anchoring members fastened to the posterior bone of the spine.

As illustrated in FIG. 1, in general terms, the present invention provides a new and improved spinal implant including a surgical mesh covering that can be anchored to bone. Although described herein for application to the spine, application to other bony anatomic structures is also included in the invention. The surgical mesh 10 has elongated slot-like anchoring members 20 which receive bone screws or other bone fasteners 30. The mesh structure may be affixed to adjacent vertebrae with the screws. The screws or other bone fasteners 30 are placed within the slot-like anchoring members 20 formed in the mesh structure which allows the mesh structure to articulate and move with respect to other mesh structures located on adjacent vertebrae. The elongated slots of the anchoring members 20 provide for variable placement of the screws 30 and are capable of permitting sliding and gliding motion of an anchoring member upon a bone fastener 30. Preferably, the anchoring member slidable receives a bone fastener, for example a bone screw or a wire. The connection of the anchoring members, also referred to herein as anchoring slots, to the bone fasteners may further include bushings to aid the sliding motion of the anchoring member on the bone fastener. The slots also may be recessed.

One embodiment of the invention comprises an implantable surgical mesh 10, having a multitude of anchoring members 20. The embodiment further includes bone fasteners 30, for example bone screws, for attaching the surgical mesh to a patient's bone. Other bone fasteners known in the art, for example wires, may also be used to connect the anchoring members to a patient's bone. As used herein, the term mesh includes, but is not limited to, a sheet-like or substantially flat and thin structure. The term mesh includes various mats and sheets of materials. In at least one preferred embodiment the mesh includes a structure with a multitude of interstices, fenestrations, or spaces penetrating across the thickness of the structure. The mesh 10 in some embodiments may resemble a screen. The fenestrations in the mesh are advantageous in permitting the drainage of blood and other fluids across the mesh, for example to avoid the formation of epidural hematomas. The mesh may also include a material that although not macroscopically fenestrated, has substantial porous characteristics. Furthermore, in yet other embodiments, the mesh may be a mat or solid sheet of material without substantial interstices or holes, and be substantially impervious to the flow of fluids across the mesh. In some embodiments, the mesh is contoured, for example curved to fit the shape of the rounded spinal canal. In at least one embodiment, hooks are disposed on the mesh to hold the muscle against the mesh following implantation in the patient.

The mesh and other elements of the present invention may be fabricated from any number of biocompatible materials. For example the mesh and other elements may be fabricated from low memory, more plastic than elastic, biocompatible materials, for example, stainless steel 316L, gold, tantalum, etc. Some embodiments of the mesh may include metals, for example, Titanium and Titanium alloys, Tantalum, stainless steels, Cobalt chrome alloys, Gold, Silver, Platinum, etc. Other embodiments of the mesh and other elements may be fabricated from biocompatible fibers, for example, carbon fibers (graphite or diamond); collagen fibers; tendon or ligament derived fibers; keratin; catgut; silk; cellulose; chitosan; suture materials, e.g., PLA/PGA and other copolymers; polyethylene; TEFLON™; polyurethanes; BIOGLASS™; hydroxyapatite and other calcium phosphate materials. In yet other embodiments, the mesh and other elements will be fabricated from or include bioabsorbable materials, for example, collagen or fascia sheets. The mesh and other elements may also be fabricated from various biocompatible silicones. The implant may be formed of a radiolucent polymer material selected from the polyaryl ether ketone family (PAEK), such as polyether ether ketone (PEEK) or polyether ketone ketone (PEKK), or other suitable biocompatible material of sufficient strength, such as titanium. One embodiment of the mesh may be fabricated from Polyether block amide (PEBA), commercially available from Atochem Polymers of Birdsboro, Pa. under the trade name PEBAX. Some elements of the implant may be include polytetrafluoroethylene (PTFE) or polyoxymethylene. Furthermore, the mesh may be fabricated from combinations of any of the above materials.

In one embodiment, the mesh 10 is substantially rigid. A rigid mesh will resist deforming forces and tend to maintain a pre-determined shape. The rigid mesh would require a moderate amount of effort to bend or shape, requiring for example the use of a plate bender in the operating room. A rigid mesh may be particularly suited for use as a hard lamina replacement, because the rigid mesh will maintain a curved shape over the neural elements and provide a hard covering over the neural elements. A rigid mesh may be useful as a spinal plate or as an artificial lamina replacement. The rigid mesh resists compression forces, distraction forces, and twisting forces. One important aspect of the invention is that it provides improved rotational stability to the spine after a laminectomy.

In yet another embodiment, the mesh 10 is a pliable mesh that is soft, flexible, and fabric-like. The pliable mesh resists distraction forces, but is easily deformed in compression. A pliable mesh is most suitable as a ligament replacement or a flexible dural covering. The pliable mesh may also be used anteriorly on the spine to help prevent extrusion of an artificial disc, for example, while permitting motion at the disc space. The pliable mesh may also be used to provide protection to the dura and neural elements during revision surgery. A pliable mesh can help to establish a plane of dissection between the dura, the overlying muscles and soft tissues, and scar tissue during re-operation or revision surgery of the spine. Some embodiments of the pliable mesh may be soft enough to be cut in the operating room with a scissor.

In still another embodiment, the mesh 10 is semi-rigid. A semi-rigid mesh is intermediate, in structural strength and flexibility, between the rigid mesh and the pliable mesh. A semi-rigid mesh resists deforming forces, but to a lesser degree than the rigid mesh. The semi-rigid mesh can be easily shaped in the operating room by the clinician, using slight effort. A semi-rigid mesh, for example, could be cut with a wire cutter and could be bent without necessarily using a plate bender. A semi-rigid mesh is advantageous in being more readily conformable to the anatomy of the individual patient. A semi-rigid mesh, in general terms, will tend to be not as thick, and more flexible than the rigid mesh. However, a semi-rigid mesh will substantially resist the forces of dissection instruments during revision surgeries, and provide greater protection to the neural elements than a pliable mesh.

Figure 2A:
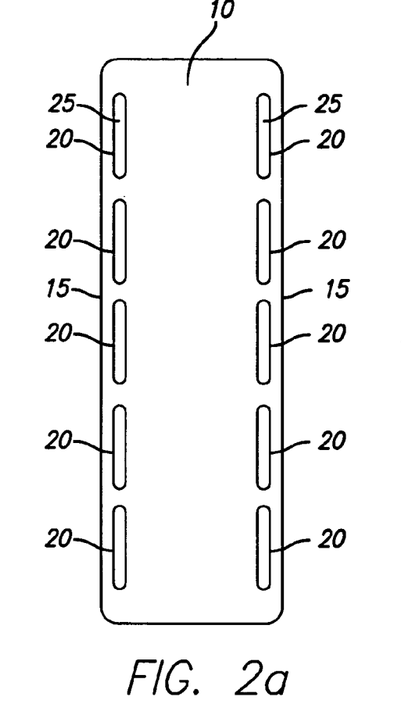
FIG. 2a is a top view of an embodiment the invention having rows of axially aligned slot-like anchoring members for receiving bone fasteners.
Figure 2B:
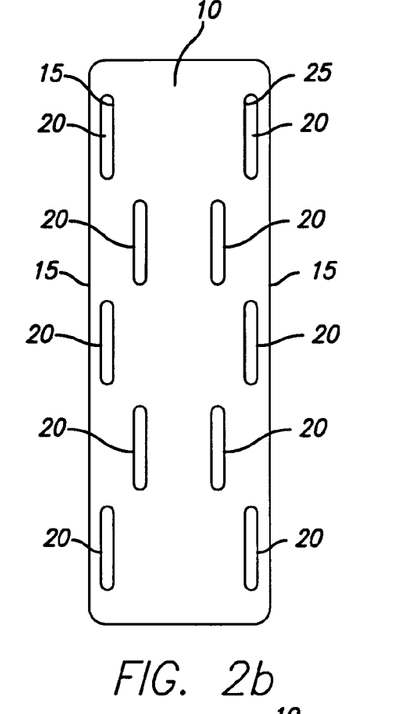
FIG. 2b is a top view of an embodiment of the invention having slot-like anchoring members spaced apart in a staggered arrangement.

Referring now to FIG. 2a and FIG. 2b, the illustrated embodiment of the invention further includes anchoring members 20 that are positioned adjacent to the two lateral edges 15 of the mesh 10. The anchoring members may be made from stainless steel, titanium alloy, or other materials known in the art for making bone screws. The lateral edges 15 of the mesh 10 need not be straight or parallel and can be curved, wavy, or contoured. The anchoring members 20 in one preferred embodiment include elongated slot-like central openings 25. As shown in FIG. 2a, the anchoring members in some embodiments line up longitudinally in a row adjacent to each lateral edge 15 of the mesh 10. As shown in FIG. 2b, in other embodiments the spacing between the various anchoring members 20 on a mesh 10 may be staggered medially to laterally, and/or longitudinally, to give the surgeon more leeway, discretion, and options for placement of the bone fasteners. The spacing apart of the anchoring members will vary to accommodate the various levels of the spine. For example, anchoring members 20 would be spaced closer together for use on the cervical spine and farther apart for use on the lumber spine because the cervical vertebra are anatomically smaller than the lumbar vertebra. Embodiments for use on the Thoracic spine will have an intermediate spacing.

Figure 3A:
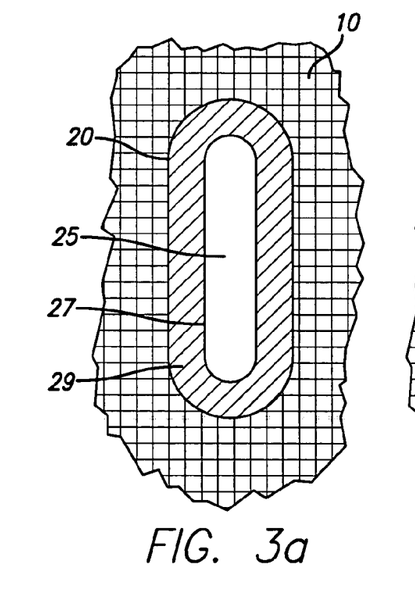
FIG. 3a is a top view of an embodiment of the invention having an anchoring member with a recessed periphery.
Figure 3B:
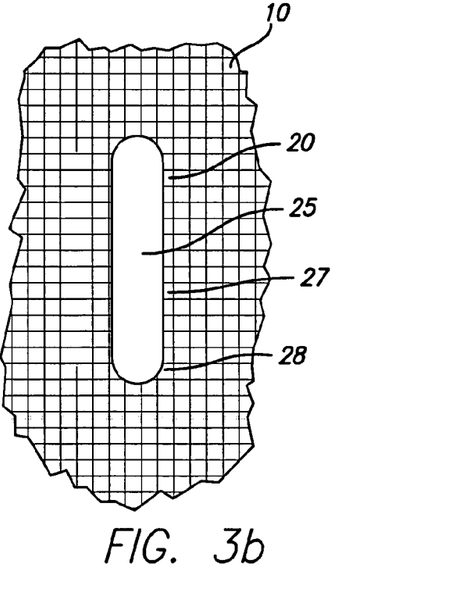
FIG. 3b is a top view of an embodiment of the invention having an anchoring member with a reinforced periphery.

Referring now also to FIG. 3a and FIG. 3b, the anchoring members 20 include an elongated slot-like central opening 25 defined by a periphery 27. In the preferred embodiment, the side walls of the periphery are substantially parallel. The size of the elongated central opening 25 varies in different embodiments. In general, the width of the elongated opening should be at least as wide as the width of the bone fastener. For example, if the bone fastener is a screw, the elongated opening of the anchoring member will be at least wide enough to allow the treaded portion of the screw to pass therethrough, but not as wide as the head of the screw. The length of the elongated openings 25 can vary from slightly greater than the width of the threaded portion of the screw to slightly less than the length of the mesh 10.

In one preferred embodiment, the elongated openings 25 of the anchoring members have a reinforced periphery 28 made of a sturdy material, for example a metal, a rigid plastic polymer, or a rigid fiber material. The reinforced periphery 28 of the anchoring members 20 may also be chosen, for example, from the various materials listed above for fabrication of the mesh. In the rigid mesh, the anchoring members may be simple elongated openings cut into the mesh material without periphery reinforcement. However in the pliant mesh, in at least one preferred embodiment, the openings of the anchoring members have the reinforced periphery. Furthermore, the anchoring members in some preferred embodiments have a recessed periphery 29, to provide a low profile to the anchoring member 20 and to the bone fastener 30. For example, the head of a bone screw 30 will fit within the recessed perimeter, so that the head of the bone screw sits flush with the surrounding mesh 10.

Figure 4:
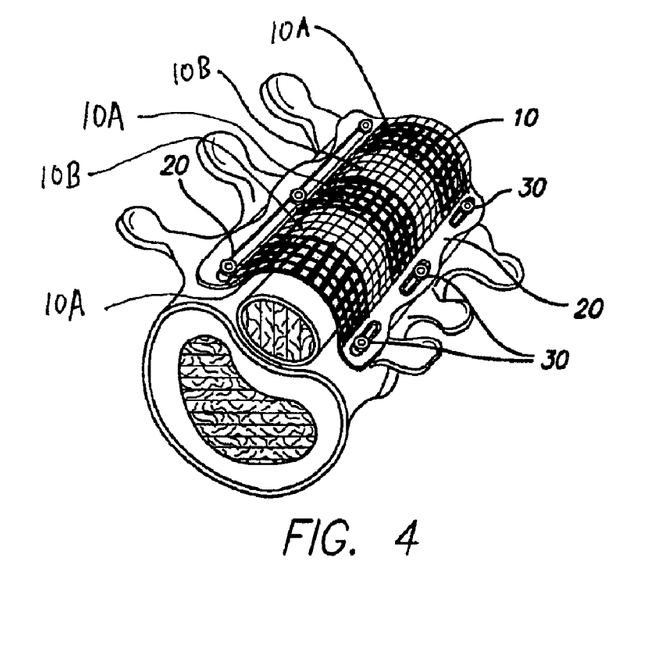
FIG. 4 is a perspective view of one embodiment of the invention having a single long slot on either side of the mesh.

One advantage of the elongated slotted anchoring members 20 is that the surgeon has more leeway, discretion, and options in positions for placement of the bone fastener 30. Patients come in different sizes with variable distances between anatomic structures. The distance from lamina to lamina, and from facet to facet varies not only from patient to patient, but also at different spinal levels within the same patient. If only a single round hole is provided for placement of a bone screw, the hole may not always fall over the anatomic location suitable for placement and purchase of the screw or bone fastener 30. The elongated slots of the anchoring members advantageously give the surgeon leeway in placing the screw. Round holes do not give any leeway in screw placement. In at least one embodiment, shown in FIG. 4, a single long anchoring member 20 is provided on each lateral side of the mesh 10, the anchoring member running almost the entire length of the mesh 10 from one end to the other. The surgeon can then place bone fasteners 30 anywhere along the length of long anchoring member 20 that spans the length of the mesh strip. Furthermore, anchoring members comprising elongated slots instead of round holes are more flexible in positioning, which means that the device can be manufactured in fewer sizes, thereby making the device more economical for surgical use.

Another advantage of the elongated slot-like anchoring members 20 is that the anchoring member may be allowed to slide or glide upon the bone fastener 30. In a preferred embodiment of the present invention, the side walls of the periphery of the anchoring members are substantially parallel to facilitate the sliding motion. The sliding can be made more efficient by including a bushing or by providing a screw shaft that is unthreaded for a distance from the head of the screw. The slidable interaction of the anchoring member 20 and the bone fastener 30 provides a degree of normal anatomic movement of the spine when the mesh is implanted. However, should the surgeon prefer, the screw can be tightened down to lock the anchoring member to the bone and to prevent sliding of the anchoring member upon the screw. An embodiment with a slidable interaction of the anchoring member and the bone fastener may be useful, for example, when using the mesh covering as an anterior cover for an artificial disc or as a posterior spinal element replacement.

The invention may further include various types of bone fasteners 30. The bone fastener passes through the anchoring member and is adapted to attach to the patient's bone. In at least one preferred embodiment, the bone fastener is a bone screw 30. The bone screw can be a cortical, a cancellous, or a cortico-cancellous screw. The bone fastener 30 may also be a locking screw. A locking screw is a screw that is capable of either locking to the bone and/or locking to the anchoring member. Locking screws known in the art are supplied with locking screw heads, or locking screw shafts. In some embodiments, the anchoring member is not tightened down to the bone, and the anchoring member is allowed to glide or slide upon the bone fastener. In still other embodiments, the anchoring member is firmly attached to the bone fastener or to the bone to prevent sliding or gliding of the anchoring member on the bone fastener. Alternative bone fasteners such as wires and staples may be used. When the mesh is used on the posterior spine, the bone fasteners may be secured, for example to remaining lamina, facets, articular processes, pedicles, or transverse processes. When the mesh is applied anteriorly, the bone fasteners can be inserted into the vertebral bodies. However, bone fasteners may be attached to any part of the bony anatomy and the above examples are illustrative only and not limiting.

For example, in some embodiments, a wire may be passed through a hole drilled in the bone and through the opening in the anchoring member 20. The free ends of the wire are then secured to each other by twisting or clamping the free ends of the wire. An elongated opening in an anchoring member will in general slide upon a wire. In yet other embodiments, a bushing is provided along with the anchoring member 20 and the bone fastener 30 in order to facilitate the gliding and sliding motion of the anchoring member on the bone fastener.

Figure 5:
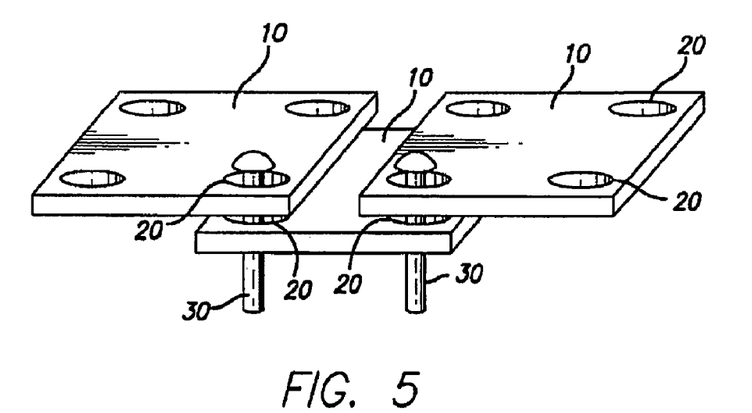
FIG. 5 is a perspective view of one embodiment of the invention showing modules stacked upon one another.

The mesh 10 may be provided in various lengths and widths. In at least one embodiment, the mesh is provided as a long strip with a multitude of anchoring members 20. The strip may be cut to a desired length in the operating room by the surgeon. In yet another embodiment, as shown in FIG. 5, the mesh 10 is provided in shorter modular strips that overlap each other. When applying modular strips of mesh, a single bone fastener 30 is passed through two overlapping anchoring members 20 from two different mesh 10 strips. The bone fastener locks the two mesh strips together. Further modular mesh strips are then added on at either end, as desired, in order to provide the desired length of dural coverage.

In yet another embodiment, the mesh includes alternating segments of rigid mesh 10A and pliable mesh 10B. The alternating segments are configured to resemble the anatomic appearance of lamina alternating with ligamentum flavum.

This artificial posterior element may be molded as one piece, or the rigid segments connected with the pliable members using well known techniques. In this embodiment, the anchoring members are preferably located on the rigid segments. Bone fasteners are passed through the anchoring members on the rigid segments and attached to the patient's bone, for example to the facet. In this embodiment, motion can occur in the pliable segments located between the rigid segments.

Figure 6:
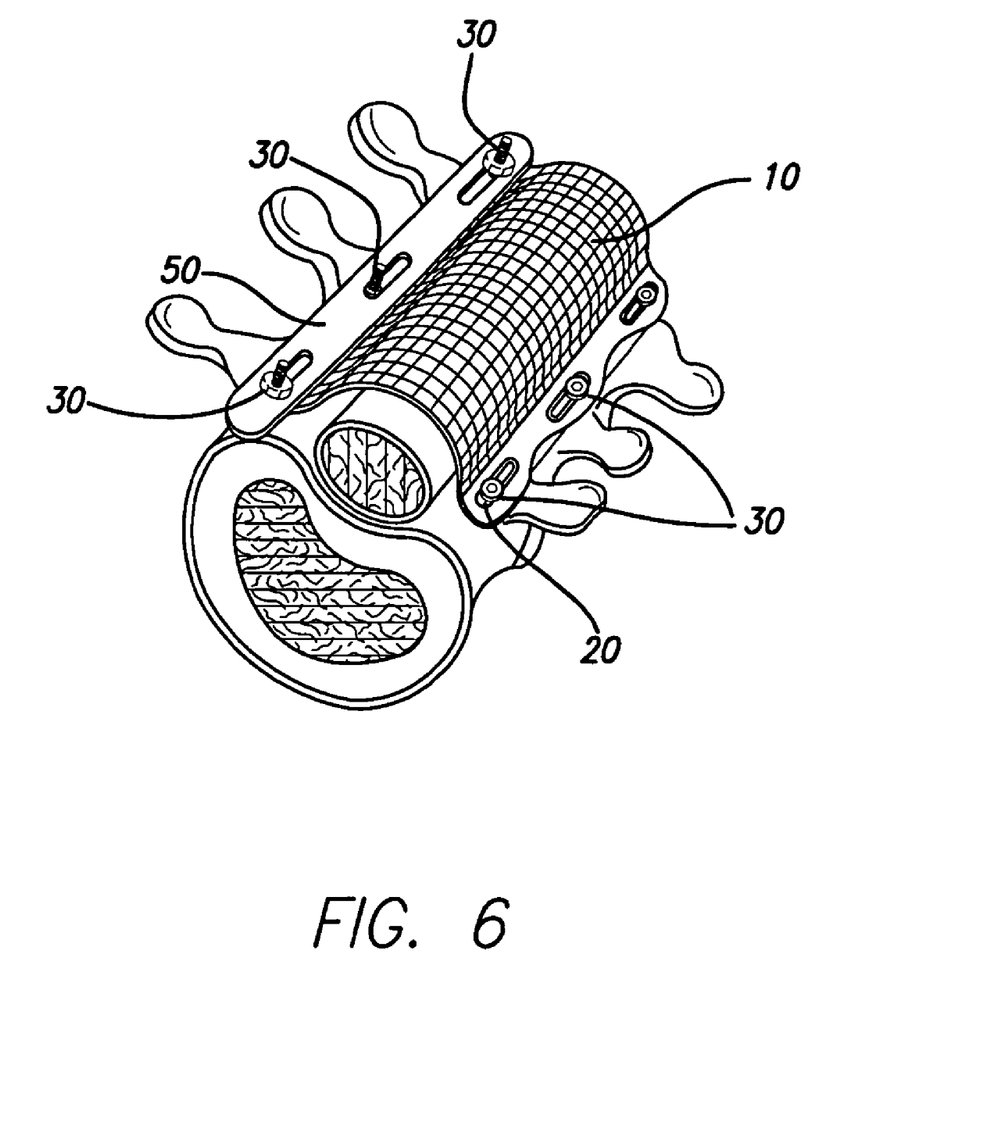
FIG. 6 is a perspective view of an embodiment of the invention including tension bands.

Referring now to FIG. 6, yet a further embodiment of the present invention is tension bands 50. The tension bands are configured to attach to two or more of the bone fasteners 30. In one embodiment the tension bands restrict distraction of one bone fastener from another bone fastener. Tension bands that restrict distraction are advantageous in restricting flexion of the spine. Such tension bands may include wires or plates composed of metals, alloys, or rigid polymers known in the art. In another embodiment, the tension bands may stretch to allow distraction of one bone fastener from another bone fastener during spinal motion. Tension bands that stretch may be useful in permitting various degrees of flexion of the spine. Such stretchable tension bands may be made of silicone or other flexible materials known in the art. The width, length, and material of the bands will determine the characteristics of rigidity, flexibility, or stretch in a band. Various combinations of bands may be used with bone fasteners alone or with bone fasteners and mesh 10 to adjust the segmental motion of the spinal segments to be treated.

In one embodiment, the tension bands 50 are configured as elongated, generally flat or generally cylindrical members. The tension bands may have a curved profile to match the lordotic curve of the normal lumbar spine. The tension bands may include holes or slots configured to accept the passage of at least one bone fastener 30 therethrough. The tension bands may be connected with the bone fasteners by sliding the tension band over the bone fastener and securing the tension band, for example with washers, clips, nuts, or wires. The tension bands may also be looped around the bone fasteners. In yet another embodiment, the tension bands may be configured to connect to the sides of an bone fastener. In other embodiments, the tension bands may be configured to fit between the anchoring members 20 and the bone to be treated or over the anchoring members.

In another embodiment, the invention comprises a surgical method for protecting the dura. The method includes providing a mesh 10 including elongated anchoring members 20, the mesh being of sufficient size to cover the laminectomy defect, disposing the mesh over the dura, passing bone fasteners 30 through the anchoring member openings, and securing the bone fasteners to the bone. The bone fasteners may be secured, for example to remaining portions of lamina, facets, articular processes, pedicles, or transverse processes. In various embodiments, the bone fasteners may be connected with the anchoring members and tightened partially to provide a sliding interaction of the anchoring member on the bone fastener, or tightened down completely to provide a non-sliding interaction of the anchoring member on the bone fastener.

In still another embodiment, the invention provides a method of performing a laminoplasty. The method comprises providing a mesh including elongated anchoring members, the mesh being of sufficient size to cover the laminectomy defect, disposing the mesh over the dura, passing bone fasteners through the anchoring member openings, securing the bone fasteners to the bone, and disposing bone graft over the mesh. In various embodiments, BMP may be placed along with or instead of the bone graft.

In yet another embodiment, the invention provides another method of performing a laminoplasty. The method comprises providing a mesh including elongated anchoring members and having alternating rigid segments and pliable segments, and connecting the anchoring members to bone with bone fasteners. Preferably, the anchoring members of the rigid segments are connected to the bone, for example to the facets.

In still another embodiment, the invention provides a method of replacing a ligament. The method comprises providing a mesh including elongated anchoring members of sufficient length to span the repair site, disposing the mesh over the repair site, passing bone fasteners through the anchoring member openings, and securing the bone fasteners to the bone.

Yet another embodiment of the present invention is a method of securing a disc implant in a disc space. In one embodiment, the invention is used in conjunction with total artificial disc replacement, for example, a Charite™ artificial disc. Artificial discs may be advantageous in treating disc disease while maintaining segmental spinal motion at the disc level that is treated. Implantation of an artificial disc anteriorly between two vertebral bodies is preferred at a spinal level that has generally intact posterior spinal elements. Intact posterior spinal elements are important in preventing excessive distraction of the disc space during placement of an artificial disc and dislocation of the artificial disc post operatively. Patients who have had lumbar laminectomy with removal of posterior elements, for example, the lamina, have therefore previously not been good candidates for total disc replacement with an artificial disc. The present invention provides posterior stability while providing generally physiologic spinal motion, whereas a spinal fusion prevents segmental spinal motion. Therefore, when used in conjunction with the present invention, a patient who has had a laminectomy may still be a candidate for artificial disc replacement. Furthermore, because aspects of the invention allow continued segmental spinal motion, accelerated degeneration of adjacent disc levels may be prevented.

The method of securing a disc implant, for example, a bone graft, cage, or an artificial disc, in a disc space includes providing a mesh including elongated anchoring members. In one embodiment, the mesh is of sufficient length to cover the implant and at least about 0.25 inch (about 0.64 cm) of bone to either side of the bone graft, connecting the anchoring members to the bone on either side of the graft using bone fasteners, and stretching the mesh longitudinally to provide tension over the bone graft. In various embodiments, the bone fasteners may be connected with the anchoring members and tightened partially to provide a sliding interaction of the anchoring member on the bone fastener, or tightened down completely to provide a non-sliding interaction of the anchoring member on the bone fastener.

In another embodiment of the invention the amount of distraction between spinal levels is restricted by connecting tension bands with bone fasteners. The tension bands may be connected by sliding the tension bands over the bone fasteners and securing the tension bands, for example with washers, clips, nuts, or wires.

The invention may be embodied in other forms without departure from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

The invention claimed is:

1. A posterior spinal implant, comprising a barrier for covering a spinal portion, the barrier having a length parallel to a longitudinal axis and a width transverse to the longitudinal axis, the barrier having rigid segments and pliable segments in an alternating configuration with one another to resemble the anatomic structure of a natural rigid lamina alternating with a pliable ligamentum flavum, the rigid segments having a length parallel to the width of the barrier and the pliable segments having a length parallel to the width of the barrier such that the rigid segments are elongated perpendicular to the longitudinal axis and the pliable segments are elongated perpendicular to the longitudinal axis, wherein the rigid segments include modular rigid mesh strips and the pliable segments include modular pliable mesh strips, the modular rigid mesh strips and the modular pliable mesh strips being discrete strips from one another, and the modular rigid mesh strips and the modular pliable mesh strips being configured to mechanically lock to one another.

2. The bone anchored device of claim 1, wherein the barrier of the posterior spinal implant is a substantially flat and thin structure.

3. The bone anchored device of claim 1, wherein the barrier of the posterior spinal implant is a mat.

4. The bone anchored device of claim 1, wherein the barrier of the posterior spinal implant is a sheet of materials.

5. The bone anchored device of claim 1, wherein the barrier of the posterior spinal implant includes a structure with a multitude of penetrating interstices across a thickness thereof.

6. The bone anchored device of claim 1, wherein the barrier of the posterior spinal implant is a screen.

7. The bone anchored device of claim 1, wherein the barrier of the posterior spinal implant is substantially porous to fluid flow.

8. The bone anchored device of claim 1, wherein the barrier of the posterior spinal implant is a solid sheet of material without substantial interstices.

9. The bone anchored device of claim 1, wherein the barrier of the posterior spinal implant is substantially impervious to fluid flow across the barrier.

10. The bone anchored device of claim 1, wherein the length and the width of the barrier are sized for covering a portion of a spinal dura.

11. The bone anchored device of claim 1, wherein the barrier has a curved portion having a hemi-cylindrical cross-section in a direction of the width transverse to the longitudinal axis.

12. The bone anchored device of claim 11, wherein the barrier has at least one anchoring portion extending outwardly from the curved portion in the direction of the width transverse to the longitudinal axis.

13. The bone anchored device of claim 11, wherein the anchoring portions extend in opposite directions.

14. The bone anchored device of claim 11, wherein the anchoring portions are substantially flat in the direction of the width transverse to the longitudinal axis.

15. The bone anchored device of claim 11, wherein the anchoring portions define at least one through hole for receiving an anchor adapted to attach the implant to underlying tissue.

16. The bone anchored device of claim 15, wherein the anchoring portions define multiple through holes.

17. The bone anchored device of claim 16, wherein the barrier includes at least one of the multiple through holes formed in opposing ones of the anchoring portions.

18. The bone anchored device of claim 17, wherein the at least one through hole is an elongated slot extending in the length-wise direction greater than half the length of the barrier.

19. The bone anchored device of claim 15, wherein the at least one through hole is elongated in a length-wise direction parallel to the longitudinal axis.

20. The bone anchored device of claim 1, wherein the modular rigid mesh strips and the modular pliable-mesh strips each have holes disposed for receiving a connecting member to mechanically lock adjacent strips to one another in an overlapping configuration.

21. The bone anchored device of claim 1, wherein the anatomic structure of the barrier resembling the pliable ligamentum flavum has a soft and flexible fabric like quality in the pliable segments and the anatomic structure of the barrier resembling the natural rigid lamina has a firm and supportive quality in the rigid segments.

22. The bone anchored device of claim 1, wherein the rigid segments provide a shield to protect a spinal dura.

23. The bone anchored device of claim 1, wherein the alternating configuration of the rigid segments and the pliable segments permit motion to occur in the pliable segments located between the rigid segments.

24. The posterior spinal implant of claim 1, further comprising a plurality of anchoring portions, each anchoring portions forming at least one opening surrounded by a periphery, wherein the at least one opening of the anchoring members is configured to slidingly connect with at, least one bone fastener.

25. The bone anchored device of claim 24, wherein the barrier of the posterior spinal implant is fenestrated and contoured to resemble the anatomic shape of a human spinal canal.

26. The bone anchored device of claim 24, wherein the periphery of at least one of the anchoring portions member is recessed.

27. The bone anchored device of claim 24, wherein the at least one opening is elongated and configured to slidingly connect with the at least one bone fastener.

28. The bone anchored device of claim 27, wherein at least one of the anchoring portions includes a bushing to facilitate the sliding connection with the at least one bone fastener.

29. An artificial lamina replacement, comprising:
a barrier for covering a spinal portion, the barrier having a length parallel to a longitudinal axis and a width transverse to the longitudinal axis, the barrier having rigid segments alternating with pliable segments, the rigid segments having a length parallel to the width of the barrier and the pliable segments having a length parallel to the width of the barrier such that the rigid segments are elongated perpendicular to the longitudinal axis and the pliable segments are elongated perpendicular to the longitudinal axis, wherein the rigid segments include modular rigid mesh strips and the pliable segments include modular pliable mesh strips, the modular rigid mesh strips and the modular pliable mesh strips being discrete strips from one another, and the modular rigid mesh strips and the modular pliable mesh strips being configured to mechanically lock to one another; and
a plurality of anchoring portions disposed on the barrier.

30. The artificial lamina replacement of claim 29, wherein the plurality of anchoring portions are configured to allow the at least one bone fastener to pass therethrough.

31. The artificial lamina replacement of claim 29, wherein at least one of the plurality of anchoring portions is elongated and slot-like in shape, wherein the at least one of the plurality of anchoring portions is configured to slidingly connect with at least one bone fastener.

32. The artificial lamina replacement of claim 29, wherein the anchoring members are disposed on the lateral edges of the rigid segments.

33. The artificial lamina replacement of claim 29, further comprising tension bands configured to connect with at least two of the bone fasteners.

34. The artificial lamina replacement of claim 29, wherein the plurality of anchoring portions each have at least one opening surrounded by a periphery, and wherein each of the anchoring portions is configured to connect with at least one bone fastener.

35. The artificial lamina replacement of claim 29, wherein the barrier of the posterior spinal implant is a substantially flat and thin structure.

36. The artificial lamina replacement of claim 29, wherein the barrier of the posterior spinal implant is a mat.

37. The artificial lamina replacement of claim 29, wherein the barrier of the posterior spinal implant is a sheet of materials.

38. The artificial lamina replacement of claim 29, wherein the barrier of the posterior spinal implant includes a structure with a multitude of penetrating interstices across a thickness thereof.

39. The artificial lamina replacement of claim 29, wherein the barrier of the posterior spinal implant is a screen.

40. The artificial lamina replacement of claim 29, wherein the barrier of the posterior spinal implant is substantially porous to fluid flow.

41. The artificial lamina replacement of claim 29, wherein the barrier of the posterior spinal implant is a solid sheet of material without substantial interstices.

42. The artificial lamina replacement of claim 29, wherein the barrier of the posterior spinal implant is substantially impervious to fluid flow across the barrier.

43. The artificial lamina replacement of claim 29, wherein the plurality of anchoring portions each have at least one opening surrounded by a periphery.

44. The artificial lamina replacement of claim 29, wherein the length and the width of the barrier are sized for covering a portion of a spinal dura.

45. The artificial lamina replacement of claim 29, wherein the barrier resembles the anatomic structure of a natural rigid lamina alternating with a pliable ligamentum flavum.

46. The artificial lamina replacement of claim 29, wherein the rigid segments provide a shield to protect a spinal dura.

47. The artificial lamina replacement of claim 29, wherein the rigid segments alternating with the pliable segments permit motion to occur in the pliable segments located between the rigid segments.

* * * * *